(12) United States Patent
Macherla

(10) Patent No.: US 7,550,604 B2
(45) Date of Patent: Jun. 23, 2009

(54) PYRROLOTERPENES AND USE OF THE SAME AS ANTIMICROBIAL AND ANTICANCER AGENTS

(75) Inventor: Venkata Rami Reddy Macherla, San Diego, CA (US)

(73) Assignee: Nereus Pharmaceuticals, Inc., San Diego, CA (US)

( * ) Notice: Subject to any disclaimer, the term of this patent is extended or adjusted under 35 U.S.C. 154(b) by 499 days.

(21) Appl. No.: 11/205,605

(22) Filed: Aug. 17, 2005

(65) Prior Publication Data

US 2006/0052436 A1    Mar. 9, 2006

Related U.S. Application Data

(60) Provisional application No. 60/602,581, filed on Aug. 18, 2004, provisional application No. 60/608,216, filed on Sep. 9, 2004, provisional application No. 60/662,606, filed on Mar. 16, 2005.

(51) Int. Cl.
   *C07D 207/00*    (2006.01)
(52) U.S. Cl. .................................... 548/400
(58) Field of Classification Search .................. 548/400
   See application file for complete search history.

(56) References Cited

FOREIGN PATENT DOCUMENTS

JP    4095069    3/1992

OTHER PUBLICATIONS

Huddleston et al., J. Org. Chem., 2003, vol. 68, pp. 11-14, especially p. 12, Table 1.*
Huddleston et al., J. Org. Chem., 2003, vol. 68, pp. 11-14, esp. p. 12.*
Badar et al., "Natural and Synthetic Pyrrol-2-ylpolyenes", JCS Perkin Trans I, (1973) 1416-1424.
Kato, et al., "Pyrrolostatin, A Novel Lipid Peroxidiation Inhibitor," J. Antibiotic 46 (1993) 892-899.
Yamagishi, et al., "Rumbrin, A New Cytoprotective Substance Produced by *Auxarthron unbrinum*," J. Antibiotic 46 (1993) 884.
Yamagishi, et al., "Rumbrin, A New Cytoprotective Substance Produced by *Auxarthron unbrinum*," J. Antibiotic 46 (1993) 888.
Hofle et al., "Keronopsins A and B, Chemical Defence Substances of the Marine Ciliate *Pseudokeronopsis rubra* . . . ," Angew. Chem. Int. Ed. Engl. 33 (1994) 1495-1497.
Hosoe, et al., "Three pyrrolyloctatetraenyl-α-pryones from *Auxarthron conjugatum*," Phytochem. 52 (1999) 459.
Murenets et al., "Cafamycin, a novel pyrrol ether antibiotic," Antibio. Med Biotekhnol 32 (1987) 811.
Chaney et al., "The Structure of A23187, a Divalent Cation Ionophore," J. American Chem. Soc. 96 (1974) 1932.
Klika et al., "Frankiamide, a Hightly Unususal Macrocycle . . . ," J. Organic Chem. 66 (2001) 4065.
Numata et al., "Penochalasins, a novel class of cytotoxic cytochalasans . . . ," JCS Perkin Trans I, (1996) 239.
Luibrand et al., "Ilimaquinone, A Sesquiterpenoid Quinone from a Marine Sponge," Tetrahedron 35 (1979) 609-612.
Takizawa et al., "Complete Vesiculation of Golgi Membranes . . . ,"Cell 73 (1993) 1079-1090.
Funayama et al., "Structures of Novel Antibiotics, Furaquinocins A and B," Tetrahedron Lett. 30 (1989) 7427-7430.
Pathirana et al., "Marinone and Debromomarinone: Antibiotic Sesquiterpenoid . . . ," Tetrahedron Lett. 33 (1992) 7663-7666.
Hamano et al., "Biosynthesis and Structural Revision of Neomarinone," Org. Lett. 5 (2003) 4449-4452.
Harborne, "Anthocyanins and other flavonoids," Nat. Prod. Rep. 15 (1998) 631-651.
Venkatesham et al., "New 5-Alkylpyrrole-2-carboxaldehyde Derivatives . . . ," J. Nat. Prod. 58 (2000) 1318-1320.

* cited by examiner

*Primary Examiner*—Golam M. M. Shameem
*Assistant Examiner*—Susannah Chung
(74) *Attorney, Agent, or Firm*—Knobbe, Martens, Olson & Bear LLP

(57) ABSTRACT

Disclosed herein are novel pyrroloterpene compounds and methods for obtaining these compounds. Also disclosed are methods of treating cancer and bacterial infections using the novel pyrroloterpene compounds.

11 Claims, No Drawings

PYRROLOTERPENES AND USE OF THE SAME AS ANTIMICROBIAL AND ANTICANCER AGENTS

RELATED APPLICATIONS

This application claims priority to U.S. Provisional Application Nos. 60/602,581, filed Aug. 18, 2004; 60/608,216, filed Sep. 9, 2004; and 60/662,606, filed Mar. 16, 2005, all of which are incorporated herein by reference in their entirety.

BACKGROUND OF THE INVENTION

1. Field of the Invention

The present invention relates to compounds and methods for obtaining such compounds in the fields of chemistry and medicine. More specifically, the present invention relates to compounds and procedures for making compounds useful in the treatment of cancer and the treatment of bacterial infections.

2. Description of the Related Art

Cancer is a leading cause of death in the United States. Despite significant efforts to find new approaches for treating cancer, the primary treatment options remain surgery, chemotherapy and radiation therapy, either alone or in combination. Surgery and radiation therapy, however, are generally useful only for fairly defined types of cancer, and are of limited use for treating patients with disseminated disease. Chemotherapy is the method that is generally useful in treating patients with metastatic cancer or diffuse cancers such as leukemias. Although chemotherapy can provide a therapeutic benefit, it often fails to result in cure of the disease due to the patient's cancer cells becoming resistant to the chemotherapeutic agent. Due, in part, to the likelihood of cancer cells becoming resistant to a chemotherapeutic agent, such agents are commonly used in combination to treat patients.

Similarly, infectious diseases caused, for example, by bacteria are becoming increasingly difficult to treat and cure. For example, more and more microorganisms, such as bacteria, are developing resistance to current antibiotics and chemotherapeutic agents. Examples of such bacteria include both gram positive and gram negative bacteria, including *Staphylococcus, Streptococcus, Mycobacterium, Enterococcus, Corynebacterium, Borrelia, Bacillus, Chlamidia, Mycoplasma*, and the like. Examples of Fungi include *Aspergillus, Candida, Trichoderma*, and the like. Examples of protozoa include *Plasmodium* and *Acanthamoeba*.

Therefore, a need exists for additional chemotherapeutics and antimicrobial agents to treat cancer and infectious disease. A continuing effort is being made by individual investigators, academia and companies to identify new, potentially useful chemotherapeutic and antimicrobial agents.

Marine-derived natural products are a rich source of potential new anti-cancer agents and anti-microbial agents. The oceans are massively complex and house a diverse assemblage of microbes that occur in environments of extreme variations in pressure, salinity, and temperature. Marine microorganisms have therefore developed unique metabolic and physiological capabilities that not only ensure survival in extreme and varied habitats, but also offer the potential to produce metabolites that would not be observed from terrestrial microorganisms (Okami, Y. 1993 *J Mar Biotechnol* 1:59). Representative structural classes of such metabolites include terpenes, peptides, polyketides, and compounds with mixed biosynthetic origins. Many of these molecules have demonstrable anti-tumor, anti-bacterial, anti-fungal, anti-inflammatory or immunosuppressive activities (Bull, A. T. et al. 2000 *Microbiol Mol Biol Rev* 64:573; Cragg, G. M. & D. J. Newman 2002 *Trends Pharmacol Sci* 23:404; Kerr, R. G. & S. S. Kerr 1999 *Exp Opin Ther Patents* 9:1207; Frenz, J. L., Kohl, A. C. & R. G. Kerr 2004 *Exp Opin Ther Patents* 14:17; Moore, B. S 1999 *Nat Prod Rep* 16:653; Faulkner, D. J. 2001 *Nat Prod Rep* 18:1; Mayer, A. M. & V. K. Lehmann 2001 *Anticancer Res* 21:2489), validating the utility of this source for isolating invaluable therapeutic agents. Further, the isolation of novel anti-cancer and anti-microbial agents that represent alternative mechanistic classes to those currently on the market will help to address resistance concerns, including any mechanism-based resistance that may have been engineered into pathogens for bioterrorism purposes.

SUMMARY OF THE INVENTION

In one aspect, the invention is a compound having the structure of Formula (I) and acid-addition salts and pro-drug esters thereof:

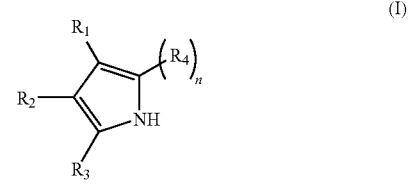

where $R_1$, $R_2$, and $R_3$ are separately selected from the group consisting of a hydrogen atom, halogen atom, mono-substituted, poly-substituted and unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, and halogenated alkyl including polyhalogenated alkyl; $(R_4)_n$ is a multiple-unit chain and $R_4$ for each unit is an isoprene separately selected from the group consisting of:

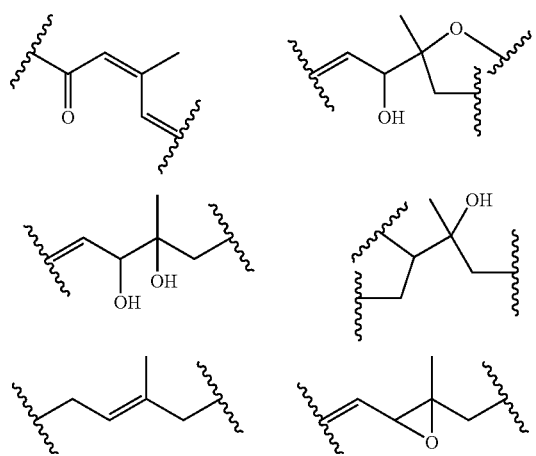

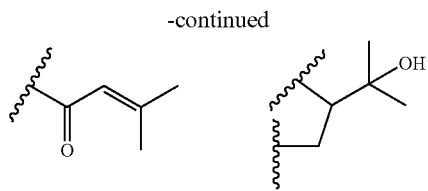 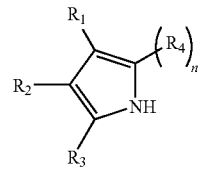

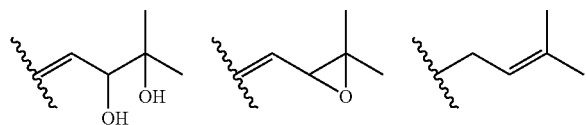

and n is an integer greater than 2. In some embodiments, $R_4$ for the first unit is:

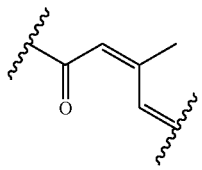

In some embodiments, the compound of formula I is selected from the group of structures consisting of:

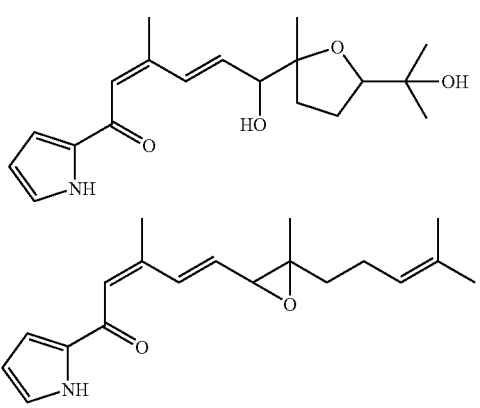

In another aspect, the invention is a compound having the structure of Formula (I) and acid-addition salts and pro-drug esters thereof:

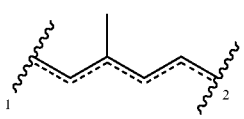
(I)

where $R_1$, $R_2$, and $R_3$ are separately selected from the group consisting of a hydrogen atom, halogen atom, mono-substituted, poly-substituted and unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, and halogenated alkyl including polyhalogenated alkyl; $(R_4)_n$ is a multiple-unit chain and $R_4$ for each unit is separately selected and has the structure of Formula (IA):

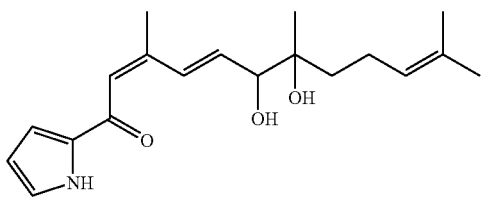
(IA)

and is optionally functionalized with hydroxy, oxo, epoxy, ether, cyclic ether, and carbonyl groups and wherein $R_4$ for the first unit is attached to the structure of Formula (I) via either attachment point 1 or 2 and $R_4$ for each additional unit is attached to the previous unit via either attachment point 1 or 2; n is an integer greater than 2; a bond represented by a dashed and solid line is either a carbon-carbon single bond or a carbon-carbon double bond; and any bond represented by a dashed and solid line that is a carbon-carbon double bond has a configuration selected from the group consisting of cis and trans.

In another aspect, the invention is a compound having the structure of Formula (II) and acid-addition salts and pro-drug esters thereof:

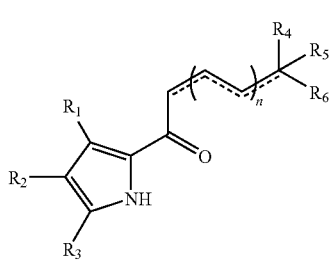
(II)

where $R_1$, $R_2$, and $R_3$ are separately selected from the group consisting of a hydrogen atom, halogen atom, mono-substituted, poly-substituted or unsubstituted variants of the following residues: saturated $C_1$-$C_{24}$ alkyl, unsaturated $C_2$-$C_{24}$ alkenyl and $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, and halogenated alkyl including polyhalogenated alkyl; $R_4$, $R_5$, and $R_6$ are separately selected from the group consisting of a hydrogen atom, halogen atom, methyl, hydroxy, oxo, ether, and carboxy groups or are separately absent; each repeated unit n is optionally functionalized with methyl, hydroxy, oxo, epoxy, ether, cyclic ether, and carboxy groups; n is an integer greater than 0; a bond represented by a dashed and solid line is either a carbon-carbon single bond or a carbon-carbon double bond; and any bond represented by a dashed and solid line that is a carbon-carbon double bond has a configuration selected from the group consisting of cis and trans.

In another aspect, the invention is a compound having the structure of Formula (III) and acid-addition salts and pro-drug esters thereof:

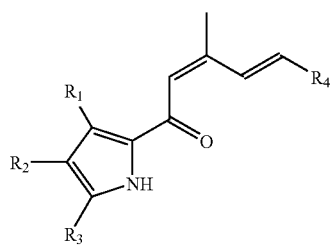

(III)

where $R_1$, $R_2$, and $R_3$ are separately selected from the group consisting of a hydrogen atom, halogen atom, mono-substituted, poly-substituted and unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, and halogenated alkyl including polyhalogenated alkyl; and $R_4$ is a seven carbon alkyl or alkenyl optionally functionalized with methyl, hydroxy, oxo, epoxy, ether, cyclic ether, and carboxy groups.

Another aspect of the invention is a method of treating cancer, comprising: administering to an individual a compound selected from the group consisting of the compounds of formulas I, II, and III, their acid-addition salts, and pro-drug esters.

Another aspect of the invention is a method of inhibiting growth of cancer cells comprising contacting a cancer cell with a compound selected from the group consisting of the compounds of formulas I, II, and III.

Another aspect of the invention is a method of treating cancer comprising contacting a patient diagnosed with cancer with a compound selected from the group consisting of the compounds of formulas I, II, and III.

Another aspect of the invention is a method of treating an individual infected with a bacteria, comprising: administering to the individual a compound selected from the group consisting of the compounds of formulas I, II, and III, their acid-addition salts, and pro-drug esters.

Another aspect of the invention is a method of inhibiting bacterial growth, comprising contacting a bacteria with a compound selected from the group consisting of the compounds of formulas I, II, and III.

Another aspect of the invention is a method of treating an individual infected with a bacteria, comprising contacting a patient diagnosed with the infection with a compound selected from the group consisting of the compounds of claims formulas I, II, and III.

DETAILED DESCRIPTION OF THE PREFERRED EMBODIMENT

Numerous references are cited herein. The references cited herein, including the U.S. patents cited herein, are to be each considered incorporated by reference in their entirety into this specification.

Embodiments of the invention include, but are not limited to providing a method for the preparation of compounds, including novel compounds, and to providing a method for producing pharmaceutically acceptable anti-tumor compositions, and anti-infectious disease compositions, for example. The methods can include the compositions in relatively high yield, wherein the compounds and/or their derivatives are among the active ingredients in these compositions. Other embodiments relate to providing novel compounds not obtainable by currently available methods. Furthermore, some embodiments relate to methods of treating cancer and infectious diseases. In preferred embodiments animal cancer and animal infectious diseases are treated by administering an effective amount of a member of a class of new compounds. Preferred embodiments relate to the compounds and methods of making and using such compounds disclosed herein, but these objectives are not necessarily met in all embodiments of the present invention.

In one embodiment, the invention provides compounds, pharmaceutical compositions, methods of producing compounds, and methods of treating cancer and microbial infections by administering compounds and compositions, wherein the compounds are represented by Formula (I):

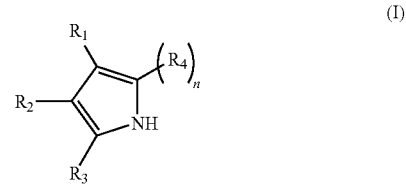

(I)

where $R_1$, $R_2$, and $R_3$ are separately selected from the group consisting of a hydrogen atom, halogen atom, mono-substituted, poly-substituted, and unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, and halogenated alkyl including polyhalogenated alkyl.

In some embodiments of the compound of Formula (I), $(R_4)_n$ is a multiple-unit chain and $R_4$ for each unit is an isoprene separately selected from the group consisting of:

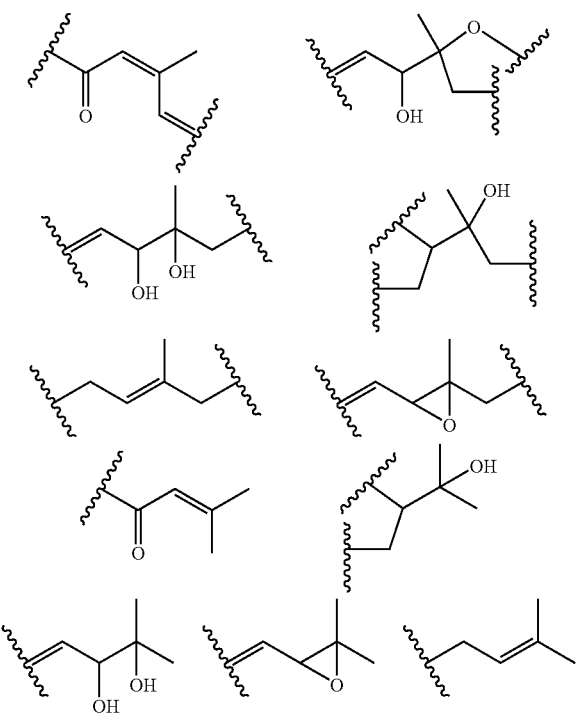

In general n can be any integer greater than 2. In some embodiments, n is 3, 4, 5, 6, 7, 8, 9, or 10. In one embodiment, n is 3.

In some embodiments of the compound of Formula (I), $R_4$ for the first unit is:

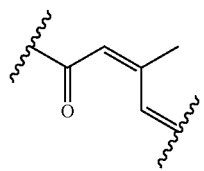

Some embodiments of the compound of Formula (I) include the structures of Formulas (IV), (V), and (VI):

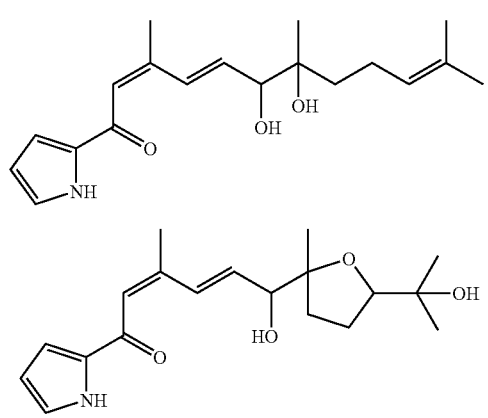

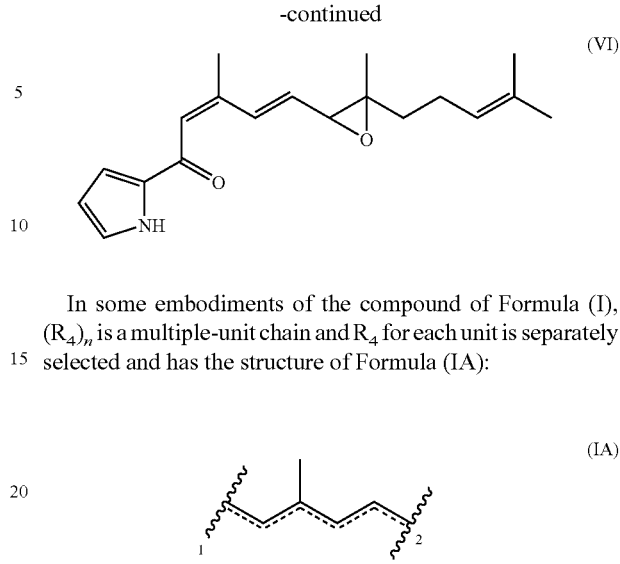

In some embodiments of the compound of Formula (I), $(R_4)_n$ is a multiple-unit chain and $R_4$ for each unit is separately selected and has the structure of Formula (IA):

(IA)

and is optionally functionalized with hydroxy, oxo, epoxy, ether, cyclic ether, and carbonyl groups. When $R_4$ is functionalized with epoxy or cyclic ether groups, the oxygen atom may form a bridge between two of the carbon atoms in $R_4$ for a given unit, thus, heterocyclizing $R_4$ for that unit. Alternatively, the oxygen atom can form a bridge between a carbon atom in $R_4$ for one unit and a carbon atom in $R_4$ for another unit. $R_4$ for the first unit may be attached to the structure of Formula (I) via either attachment point 1 or 2. Similarly, $R_4$ for each additional unit may be attached to the previous unit via either attachment point 1 or 2.

In general n can be any integer greater than 2. In some embodiments, n is 3, 4, 5, 6, 7, 8, 9, or 10. In one embodiment, n is 3. Each bond represented by a dashed and solid line is either a carbon-carbon single bond or a carbon-carbon double bond and if a carbon-carbon double bond, can have either a cis or trans configuration.

In some embodiments of the compound of Formula (I), the $R_4$ units having the structure of Formula (IA) may be chosen such that the compound of Formula (I) has one of structures of Formulas (IV), (V), and (VI):

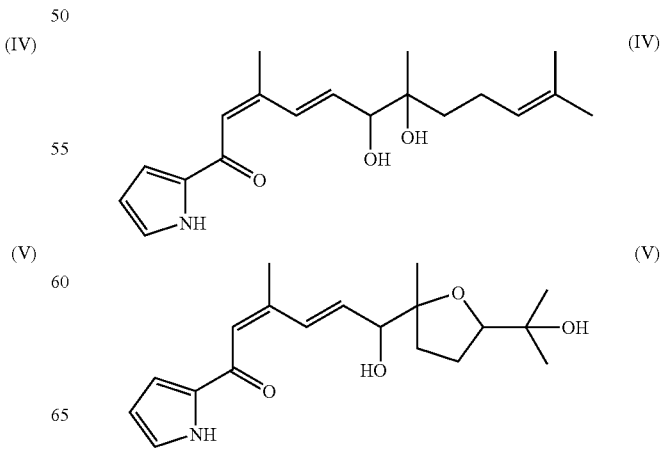

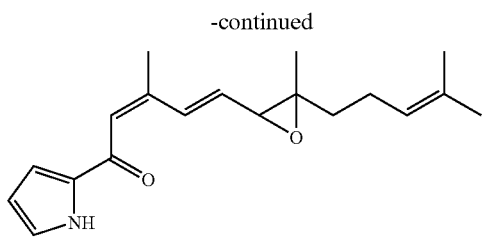

(VI)

In another embodiment, the invention provides compounds, pharmaceutical compositions, methods of producing compounds, and methods of treating cancer and microbial infections by administering compounds and compositions, wherein the compounds are represented by Formula (II):

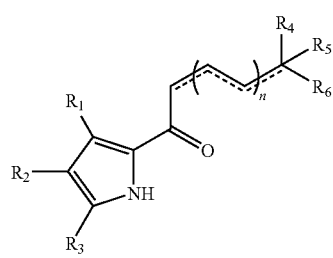

(II)

where $R_1$, $R_2$, $R_3$ are separately selected from the group consisting of a hydrogen atom, halogen atom, mono-substituted, poly-substituted or unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, and halogenated alkyl including polyhalogenated alkyl. $R_4$, $R_5$, and $R_6$ are separately selected from the group consisting of a hydrogen atom, halogen atom, methyl, hydroxy, oxo, ether, and carboxy groups or may be separately absent to accommodate a carbon-carbon double bond.

Each repeated unit n in the compound of Formula (II) is also optionally functionalized with methyl, hydroxy, oxo, epoxy, ether, cyclic ether, and carboxy groups. When the functionalization is with epoxy or cyclic ether groups, the oxygen atom forms a bridge between the two carbon atoms of a repeated unit or forms a bridge between a carbon atom of one repeated unit and a carbon atom of another repeated unit.

In the compound of Formula (II), n is an integer greater than 0. In some embodiments, n is 1, 2, 3, 4, 5, 6, 7, 8, 9, or 10. In one embodiment, n is 4.

In the compound of Formula (II), each bond represented by a dashed and solid line is either a carbon-carbon single bond or a carbon-carbon double bond and if a carbon-carbon double bond, can have either a cis or trans configuration.

In some embodiments of the compound of Formula (II), $R_1$, $R_2$, and $R_3$ are hydrogen.

Some embodiments of the compound of Formula (II) include the structures of Formulas (IV), (V), and (VI):

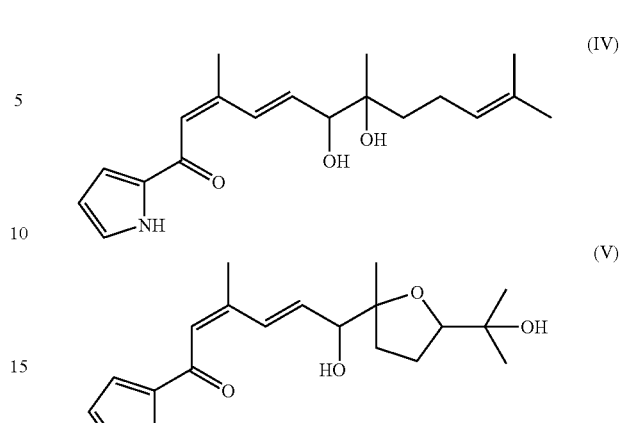

In another embodiment, the invention provides compounds, pharmaceutical compositions, methods of producing compounds, and methods of treating cancer and microbial infections by administering compounds and compositions, wherein the compounds are represented by Formula (III):

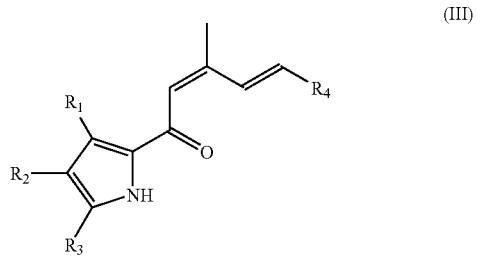

(III)

where $R_1$, $R_2$, and $R_3$ are separately selected from the group consisting of a hydrogen atom, halogen atom, mono-substituted, poly-substituted and unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, and halogenated alkyl including polyhalogenated alkyl. $R_4$ is a seven carbon alkyl or alkenyl optionally functionalized with methyl, hydroxy, oxo, epoxy, ether, cyclic ether, and carboxy groups. When $R_4$ is an alkenyl, it may have 1, 2, 3, 4, 5, or 6 carbon-carbon double bonds. Each carbon-carbon double bond may have either a cis or trans configuration. $R_4$ may consist of either a branched or a straight-chained seven-carbon alkyl or alkenyl. When $R_4$ is functionalized with epoxy or cyclic ether groups, the oxygen atom forms a bridge between two of the carbon atoms in $R_4$. In some embodiments $R_4$ is selected from the group of structures consisting of:

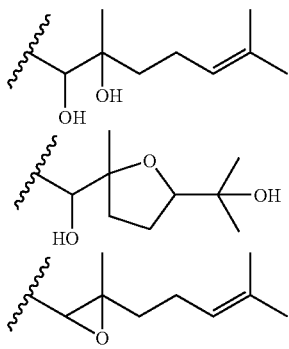

In some embodiments of the compound of Formula (III), $R_1$, $R_2$, and $R_3$ are hydrogen.

In some embodiments, pharmaceutically acceptable salts or pro-drug esters of the compounds of Formulas (I)-(VI) and methods of obtaining and purifying such compounds by the methods are provided.

The term "pro-drug ester," especially when referring to a pro-drug ester of the compounds of Formulas (I)-(VI) obtained by the methods disclosed herein, refers to a chemical derivative of the compound that is rapidly transformed in vivo to yield the compound, for example, by hydrolysis in blood or inside tissues. The term "pro-drug ester" refers to derivatives of the compounds disclosed herein formed by the addition of any of several ester-forming groups that are hydrolyzed under physiological conditions. Examples of pro-drug ester groups include pivoyloxymethyl, acetoxymethyl, phthalidyl, indanyl and methoxymethyl, as well as other such groups known in the art, including a (5-R-2-oxo-1,3-dioxolen-4-yl)methyl group. Other examples of pro-drug ester groups can be found in, for example, T. Higuchi and V. Stella, in "Pro-drugs as Novel Delivery Systems", Vol. 14, A.C.S. Symposium Series, American Chemical Society (1975); and "Bioreversible Carriers in Drug Design: Theory and Application", edited by E. B. Roche, Pergamon Press: New York, 14-21 (1987) (providing examples of esters useful as prodrugs for compounds containing carboxyl groups). Each of the above-mentioned references is herein incorporated by reference in their entirety.

The term "pharmaceutically acceptable salt," as used herein, and particularly when referring to a pharmaceutically acceptable salt of a compound, including compounds of Formulas (I)-(VI) obtained by the methods disclosed herein, refers to any pharmaceutically acceptable salts of a compound, and preferably refers to an acid addition salt of a compound. Some examples of pharmaceutically acceptable salts are the alkali metal salts (sodium or potassium), the alkaline earth metal salts (calcium or magnesium), or ammonium salts derived from ammonia or from pharmaceutically acceptable organic amines, for example $C_1$-$C_7$ alkylamine, cyclohexylamine, triethanolamine, ethylenediamine or tris-(hydroxymethyl)-aminomethane. With respect to compounds obtained by the method of the invention that are basic amines, the preferred examples of pharmaceutically acceptable salts are acid addition salts of pharmaceutically acceptable inorganic or organic acids, for example, hydrohalic, sulfuric, phosphoric acid or aliphatic or aromatic carboxylic or sulfonic acid, for example acetic, succinic, lactic, malic, tartaric, citric, ascorbic, nicotinic, methanesulfonic, p-toluensulfonic or naphthalenesulfonic acid.

Preferred pharmaceutical compositions disclosed herein include pharmaceutically acceptable salts and pro-drug esters of the compounds of Formulas (I)-(VI) obtained and purified by the methods disclosed herein. Accordingly, if the manufacture of pharmaceutical formulations involves intimate mixing of the pharmaceutical excipients and the active ingredient in its salt form, then it is preferred to use pharmaceutical excipients which are non-basic, that is, either acidic or neutral excipients.

The term "halogen atom," as used herein, means any one of the radio-stable atoms of column 7 of the Periodic Table of the Elements, i.e., fluorine, chlorine, bromine, or iodine, with fluorine and chlorine being preferred.

The term "alkyl," as used herein, means any unbranched or branched, substituted or unsubstituted, saturated hydrocarbon, with $C_1$-$C_6$ unbranched, saturated, unsubstituted hydrocarbons being preferred, with methyl, ethyl, isobutyl, and tert-butyl being most preferred. Among the substituted, saturated hydrocarbons, $C_1$-$C_6$ mono- and di- and per-halogen substituted saturated hydrocarbons and amino-substituted hydrocarbons are preferred, with perfluromethyl, perchloromethyl, perfluoro-tert-butyl, and perchloro-tert-butyl being the most preferred. The term "substituted" has its ordinary meaning, as found in numerous contemporary patents from the related art. See, for example, U.S. Pat. Nos. 6,509,331; 6,506,787; 6,500,825; 5,922,683; 5,886,210; 5,874,443; and 6,350,759; all of which are incorporated herein in their entireties by reference. Specifically, the definition of substituted is as broad as that provided in U.S. Pat. No. 6,509,331, which defines the term "substituted alkyl" such that it refers to an alkyl group, preferably of from 1 to 10 carbon atoms, having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyacylamino, cyano, halogen, hydroxyl, carboxyl, carboxylalkyl, keto, thioketo, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl. The other above-listed patents also provide standard definitions for the term "substituted" that are well-understood by those of skill in the art. The term "cycloalkyl" refers to any non-aromatic hydrocarbon ring, preferably having five to twelve atoms comprising the ring. The term "acyl" refers to alkyl or aryl groups derived from an oxoacid, with an acetyl group being preferred.

The term "alkenyl," as used herein, means any unbranched or branched, substituted or unsubstituted, unsaturated hydrocarbon including polyunsaturated hydrocarbons, with $C_1$-$C_6$ unbranched, mono-unsaturated and di-unsaturated, unsubstituted hydrocarbons being preferred, and mono-unsaturated, di-halogen substituted hydrocarbons being most preferred. The term "cycloalkenyl" refers to any non-aromatic hydrocarbon ring, preferably having five to twelve atoms comprising the ring.

The terms "aryl," "substituted aryl," "heteroaryl," and "substituted heteroaryl," as used herein, refer to aromatic hydrocarbon rings, preferably having five, six, or seven atoms, and most preferably having six atoms comprising the ring. "Heteroaryl" and "substituted heteroaryl," refer to aromatic hydrocarbon rings in which at least one heteroatom, e.g., oxygen, sulfur, or nitrogen atom, is in the ring along with at least one carbon atom. The substituted aryls and heteroaryls can be substituted with any substituent, including those described above and those known in the art.

The term "alkoxy" refers to any unbranched, or branched, substituted or unsubstituted, saturated or unsaturated ether, with $C_1$-$C_6$ unbranched, saturated, unsubstituted ethers being preferred, with methoxy being preferred, and also with dimethyl, diethyl, methyl-isobutyl, and methyl-tert-butyl ethers also being preferred. The term "cycloalkoxy" refers to any non-aromatic hydrocarbon ring, preferably having five to twelve atoms comprising the ring.

The terms "purified," "substantially purified," and "isolated" as used herein refer to the compounds of the invention being free of other, dissimilar compounds with which the compounds of the invention are normally associated in their natural state, so that the compounds of the invention comprise at least 0.5%, 1%, 5%, 10%, or 20%, and most preferably at least 50% or 75% of the mass, by weight, of a given sample.

The compounds of Formulas (I)-(VI) may be obtained and purified as set forth below.

Producing Organisms

One microorganism which may be used for the production of the compounds disclosed herein is a strain isolated from a marine sediment sample collected in Alaska. The culture (strain NPS008187) was deposited on Feb. 11, 2004 with the American Type Culture Collection (ATCC) in Rockville, Md. and assigned the ATCC patent deposition number PTA-5810. The ATCC deposit meets all of the requirements of the Budapest treaty. The culture is also maintained at and available from Nereus Pharmaceutical Culture Collection at 10480 Wateridge Circle, San Diego, Calif. 92121. In addition to the specific microorganism described herein, it should be understood that mutants, such as those produced by the use of chemical or physical mutagens including X-rays, etc. and organisms whose genetic makeup has been modified by molecular biology techniques, may also be cultivated to produce the compounds disclosed herein.

Fermentation of Strain NPS008187

The production of the compounds disclosed herein may be carried out by cultivating strain NPS008187 in a suitable nutrient medium under conditions described herein, preferably under submerged aerobic conditions, until a substantial amount of compounds are detected in the fermentation. Harvesting is conducted by extracting the active components from the mycelial growth with a suitable solvent. The solution containing the desired components is concentrated then subjected to chromatographic separation to isolate the compounds from other metabolites also present in the cultivation medium.

Production of compounds can be achieved at temperatures conducive to satisfactory growth of the producing organism, e.g. from 16 degree C. to 40 degree C. In some embodiments fermentation is conducted at 22 degree C. to 32 degree C. The aqueous medium can be incubated for a period of time necessary to complete the production of compounds as monitored by high pressure liquid chromatography (HPLC), for example for a period of about 2 to 10 day, on a rotary shaker operating at about 50 rpm to 300 rpm. In some embodiments, the rotary shaker is operated at 150 rpm to 250 rpm.

Growth of the microorganisms may be achieved by one of ordinary skill of the art by the use of appropriate medium. Broadly, the sources of carbon include but are not limited to glucose, fructose, mannose, maltose, galactose, mannitol and glycerol, other sugars and sugar alcohols, starches and other carbohydrates, or carbohydrate derivatives such as dextran, cerelose, as well as complex nutrients such as oat flour, corn meal, millet, corn, and the like. The exact quantity of the carbon source that is utilized in the medium will depend in part, upon the other ingredients in the medium, but an amount of carbohydrate between 0.5 to 25 percent by weight of the medium can be satisfactorily used, for example. These carbon sources can be used individually or several such carbon sources may be combined in the same medium.

The sources of nitrogen include amino acids such as glycine, arginine, threonine, methionine and the like, ammonium salt, as well as complex sources such as yeast extracts, corn steep liquors, distiller solubles, soybean meal, cottonseed meal, fish meal, peptone, and the like. The various sources of nitrogen can be used alone or in combination in amounts ranging from 0.5 to 25 percent by weight of the medium, for example.

Among the nutrient inorganic salts, which can be incorporated in the culture media, are the customary salts capable of yielding sodium, potassium, magnesium, calcium, phosphate, sulfate, chloride, carbonate, and like ions. Also included are trace metals such as cobalt, manganese, iron, molybdenum, zinc, cadmium, and the like.

In some embodiments, the following is exemplary fermentation protocol is used for preparing a 10 L batch of organisms that produce one or more of the compounds disclosed herein:

1. Inoculate the starting culture or the freeze culture into 10 ml seed medium and incubate at 28 C and 250 rpm for 3 days.

2. Transfer 5 ml of the above seed culture into 100-ml seed medium in a 500-ml flask. Incubate the flasks at 28 C and 250 rpm on a rotary shaker for 3 days.

3. Inoculate 5 ml each of the second seed culture into 10 500-ml flasks containing 100 ml seed medium. Incubate these flasks at 28 C and 250 rpm on a rotary shaker for 3 days.

4. Inoculate 5 ml each of the third seed culture into 100 500-ml flasks containing 100 ml production medium. Incubate these flasks at 28° C. and 250 rpm on a rotary shaker for 7 days. Resin may or may not be added to the production culture after 4 days of incubation.

5. Extract the broth with 10 liter of ethyl acetate if no resin has been added to the production culture. If resin has been added to the production culture, extract the cell mass-resin mixture with 10 liter of ethyl acetate. The extract is dried in vacuo and the desired compounds may be isolated.

Pharmaceutical Compositions

Embodiments of the present invention also relate to the compounds disclosed herein used in pharmaceutical compositions. The compounds can optionally and preferably produced by the methods disclosed herein. The compounds can be used, for example, in pharmaceutical compositions comprising a pharmaceutically acceptable carrier prepared for storage and subsequent administration. Also, embodiments relate to a pharmaceutically effective amount of the products and compounds disclosed above in a pharmaceutically acceptable carrier or diluent. Acceptable carriers or diluents for therapeutic use are well known in the pharmaceutical art, and are described, for example, in Remington's Pharmaceutical Sciences, 18th Ed., Mack Publishing Co., Easton, Pa. (1990), which is incorporated herein by reference in its entirety. Preservatives, stabilizers, dyes and even flavoring agents may be provided in the pharmaceutical composition. For example, sodium benzoate, ascorbic acid and esters of p-hydroxybenzoic acid may be added as preservatives. In addition, antioxidants and suspending agents may be used.

Compositions of the compounds described herein may be formulated and used as tablets, capsules, or elixirs for oral administration; suppositories for rectal administration; sterile solutions, suspensions for injectable administration; patches for transdermal administration, and sub-dermal deposits and the like. Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. If desired, absorption enhancing preparations (for example, liposomes), may be utilized.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or other organic oils such as soybean, grapefruit or almond oils, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. Such formulations can be made using methods known in the art. See, for example, U.S. Pat. Nos. 5,733,888 (injectable compositions); 5,726,181 (poorly water soluble compounds); 5,707,641 (therapeutically active proteins or peptides); 5,667,809 (lipophilic agents); 5,576,012 (solubilizing polymeric agents); 5,707,615 (anti-viral formulations); 5,683,676 (particulate medicaments); 5,654,286 (topical formulations); 5,688,529 (oral suspensions); 5,445,829 (extended release formulations); 5,653,987 (liquid formulations); 5,641,515 (controlled release formulations) and 5,601,845 (spheroid formulations); all of which are incorporated herein by reference in their entireties.

Further disclosed herein are various pharmaceutical compositions well known in the pharmaceutical art for uses that include intraocular, intranasal, and intraauricular delivery.

Pharmaceutical formulations include aqueous ophthalmic solutions of the active compounds in water-soluble form, such as eyedrops, or in gellan gum (Shedden et al., *Clin. Ther.*, 23(3):440-50 (2001)) or hydrogels (Mayer et al., *Ophthalmologica*, 210(2):101-3 (1996)); ophthalmic ointments; ophthalmic suspensions, such as microparticulates, drug-containing small polymeric particles that are suspended in a liquid carrier medium (Joshi, A., *J. Ocul. Pharmacol.*, 10(1): 29-45 (1994)), lipid-soluble formulations (Alm et al., *Prog. Clin. Biol. Res.*, 312:447-58 (1989)), and microspheres (Mordenti, *Toxicol. Sci.*, 52(1):101-6 (1999)); and ocular inserts. All of the above-mentioned references, are incorporated herein by reference in their entireties. Such suitable pharmaceutical formulations are most often and preferably formulated to be sterile, isotonic and buffered for stability and comfort. Pharmaceutical compositions may also include drops and sprays often prepared to simulate in many respects nasal secretions to ensure maintenance of normal ciliary action. As disclosed in Remington's Pharmaceutical Sciences, 18th Ed., Mack Publishing Co., Easton, Pa. (1990), which is incorporated herein by reference in its entirety, and well-known to those skilled in the art, suitable formulations are most often and preferably isotonic, slightly buffered to maintain a pH of 5.5 to 6.5, and most often and preferably include antimicrobial preservatives and appropriate drug stabilizers. Pharmaceutical formulations for intraauricular delivery include suspensions and ointments for topical application in the ear. Common solvents for such aural formulations include glycerin and water.

When used as an anti-cancer or anti-microbial/infectious disease compound, the compounds of the present invention or compositions including these compounds can be administered by either oral or a non-oral pathways. When administered orally, it can be administered in capsule, tablet, granule, spray, syrup, or other such form. When administered non-orally, it can be administered as an aqueous suspension, an oily preparation or the like or as a drip, suppository, salve, ointment or the like, when administered via injection, subcutaneously, intreperitoneally, intravenously, intramuscularly, or the like. Similarly, it may be administered topically, rectally, or vaginally, as deemed appropriate by those of skill in the art for bringing the compound of the invention into optimal contact with a tumor, thus inhibiting the growth of the tumor. Local administration at the site of the cancer/tumor is also contemplated, either before or after tumor resection, as are controlled release formulations, depot formulations, and infusion pump delivery.

Methods of Administration

The present invention also encompasses methods for making and for administering the disclosed chemical compounds and the disclosed pharmaceutical compositions. Such disclosed methods include, among others, (a) administration though oral pathways, which administration includes administration in capsule, tablet, granule, spray, syrup, or other such forms; (b) administration through non-oral pathways, which administration includes administration as an aqueous suspension, an oily preparation or the like or as a drip, suppository, salve, ointment or the like; administration via injection, subcutaneously, intraperitoneally, intravenously, intramuscularly, intradermally, or the like; as well as (c) administration topically, (d) administration rectally, or (e) administration vaginally, as deemed appropriate by those of skill in the art for bringing the compound of the invention into contact with living tissue; and (f) administration via controlled released formulations, depot formulations, and infusion pump delivery. As further examples of such modes of administration and as further disclosure of modes of administration, disclosed herein are various methods for administration of the disclosed chemical compounds and pharmaceutical compositions including modes of administration through intraocular, intranasal, and intraauricular pathways.

The pharmaceutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

In practicing the methods of the invention, the products or compositions can be used alone or in combination with one another or in combination with other therapeutic or diagnostic agents. These products can be utilized in vivo, ordinarily in a mammal, preferably in a human, or in vitro. In employing them in vivo, the products or compositions can be administered to the mammal in a variety of ways, including parenterally, intravenously, subcutaneously, intramuscularly, colonically, rectally, vaginally, nasally or intraperitoneally, employing a variety of dosage forms. Such methods may also be applied to testing chemical activity in vivo.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

In non-human animal studies, applications of potential products are commenced at higher dosage levels, with dosage being decreased until the desired effect is no longer achieved or adverse side effects disappear. The dosage may range broadly, depending upon the desired affects and the therapeutic indication. Typically, dosages may be between about 10 microgram/kg and 100 mg/kg body weight, preferably between about 100 microgram/kg and 10 mg/kg body weight. Alternatively dosages may be based and calculated upon the surface area of the patient, as understood by those of skill in the art. Administration is preferably oral on a daily or twice daily basis.

The exact formulation, route of administration and dosage can be chosen by the individual physician in view of the patient's condition. See for example, Fingl et al., in The Pharmacological Basis of Therapeutics, 1975, which is incorporated herein by reference in its entirety. It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Depending on the specific conditions being treated, such agents may be formulated and administered systemically or locally. A variety of techniques for formulation and administration may be found in Remington's Pharmaceutical Sciences, 18th Ed., Mack Publishing Co., Easton, Pa. (1990), which is incorporated herein by reference in its entirety. Suitable administration routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections.

For injection, the agents of the invention may be formulated in aqueous solutions, preferably in physiologically compatible buffers such as Hanks' solution, Ringer's solution, or physiological saline buffer. For such transmucosal administration, penetrants appropriate to the barrier to be permeated are used in the formulation. Such penetrants are generally known in the art. Use of pharmaceutically acceptable carriers to formulate the compounds herein disclosed for the practice of the invention into dosages suitable for systemic administration is within the scope of the invention. With proper choice of carrier and suitable manufacturing practice, the compositions disclosed herein, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, then administered as described above. All molecules present in an aqueous solution at the time of liposome formation are incorporated into the aqueous interior. The liposomal contents are both protected from the external micro-environment and, because liposomes fuse with cell membranes, are efficiently delivered into the cell cytoplasm. Additionally, due to their hydrophobicity, small organic molecules may be directly administered intracellularly.

Determination of the effective amounts is well within the capability of those skilled in the art, especially in light of the detailed disclosure provided herein. In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions. The pharmaceutical compositions may be manufactured in a manner that is itself known, for example, by means of conventional mixing, dissolving, granulating, dragee-making, levitating, emulsifying, encapsulating, entrapping, or lyophilizing processes.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. Recognized in vitro models exist for nearly every class of condition, including the conditions abated by the compounds disclosed herein, including cancer, cardiovascular disease, and various immune dysfunction. Similarly, acceptable animal models may be used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of a compound in humans.

When used as an anti-cancer agent, a tumor-growth-inhibiting compound, or antimicrobial, the compounds disclosed herein may be administered by either oral or a non-oral pathways. When administered orally, the compounds can be administered in capsule, tablet, granule, spray, syrup, or other such form. When administered non-orally, the compounds can be administered as an aqueous suspension, an oily preparation or the like or as a drip, suppository, salve, ointment or the like, when administered via injection, subcutaneously, intraperitoneally, intravenously, intramuscularly, intradermally, or the like. Similarly, the compounds may be administered topically, rectally, or vaginally, as deemed appropriate by those of skill in the art for bringing the compound of the invention into optimal contact with a tumor, thus inhibiting the growth of the tumor. Local administration at the site of the tumor or other disease condition is also contemplated, either before or after tumor resection, or as part of an art-recognized treatment of the disease condition. Controlled release formulations, depot formulations, and infusion pump delivery are similarly contemplated.

When used as an anti-cancer agent, an anti-tumor agent, or as an antimicrobial, the compound disclosed herein may be orally or non-orally administered to a human patient in the amount of about 0.0007 mg/day to about 7,000 mg/day of the active ingredient, and more preferably about 0.07 mg/day to about 70 mg/day of the active ingredient at, preferably, one time per day or in other embodiments, over two to about ten times per day. Alternatively and also preferably, the compounds disclosed herein may be administered in the stated amounts continuously by, for example, an intravenous drip. Thus, for a patient weighing 70 kilograms, the preferred daily dose of the active ingredient would be about 0.0007 mg/kg/day to about 35 mg/kg/day, and more preferable, 0.007 mg/kg/day to about 0.035 mg/kg/day. Nonetheless, as will be understood by those of skill in the art, in certain situations it may be necessary to administer the compounds disclosed herein in amounts that excess, or even far exceed, the above-stated, preferred dosage range to effectively and aggressively treat particularly aggressive microbes or tumors.

To formulate the dosage including the compounds disclosed herein as a tumor-growth-inhibiting compound or antimicrobials, known surface active agents, excipients, smoothing agents, suspension agents and pharmaceutically acceptable film-forming substances and coating assistants, and the like may be used. Preferably alcohols, esters, sulfated aliphatic alcohols, and the like may be used as surface active agents; sucrose, glucose, lactose, starch, crystallized cellulose, mannitol, light anhydrous silicate, magnesium aluminate, magnesium methasilicate aluminate, synthetic aluminum silicate, calcium carbonate, sodium acid carbonate, calcium hydrogen phosphate, calcium carboxymethyl cellulose, and the like may be used as excipients; magnesium stearate, talc, hardened oil and the like may be used as smoothing agents; coconut oil, olive oil, sesame oil, peanut oil, soya may be used as suspension agents or lubricants; cellulose acetate phthalate as a derivative of a carbohydrate such as cellulose or sugar, or methylacetate-methacrylate copolymer as a derivative of polyvinyl may be used as suspension agents; and plasticizers such as ester phthalates and the like may be used as suspension agents. In addition to the foregoing preferred ingredients, sweeteners, fragrances, colorants, preservatives and the like may be added to the administered formulation of the compound of the invention, particularly when the compound is to be administered orally.

The pharmaceutical compositions disclosed herein may also comprise a pharmaceutically acceptable carrier. Such compositions may be prepared for storage and for subsequent administration. Acceptable carriers or diluents for therapeutic use are well known in the pharmaceutical art, and are described, for example, in Remington's Pharmaceutical Sciences, 18th Ed., Mack Publishing Co., Easton, Pa. (1990), which is incorporated herein by reference in its entirety. For example, such compositions may be formulated and used as tablets, capsules or solutions for oral administration; suppositories for rectal or vaginal administration; sterile solutions or suspensions for injectable administration. Injectables can be prepared in conventional forms, either as liquid solutions or suspensions, solid forms suitable for solution or suspension in liquid prior to injection, or as emulsions. Suitable excipients include, but are not limited to, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. If desired, absorption enhancing preparations (for example, liposomes), may be utilized.

The pharmaceutically effective amount of the composition required as a dose will depend on the route of administration, the type of animal being treated, and the physical characteristics of the specific animal under consideration. The dose can be tailored to achieve a desired effect, but will depend on such factors as weight, diet, concurrent medication and other factors which those skilled in the medical arts will recognize.

The products or compositions of the invention, as described above, may be used alone or in combination with one another, or in combination with other therapeutic or diagnostic agents. These products can be utilized in vivo or in vitro. The useful dosages and the most useful modes of administration will vary depending upon the age, weight and animal treated, the particular compounds employed, and the specific use for which these composition or compositions are employed. The magnitude of a dose in the management or treatment for a particular disorder will vary with the severity of the condition to be treated and to the route of administration, and depending on the disease conditions and their severity, the compositions may be formulated and administered either systemically or locally. A variety of techniques for formulation and administration may be found in Remington's Pharmaceutical Sciences, 18th Ed., Mack Publishing Co., Easton, Pa. (1990), which is incorporated herein by reference in its entirety.

To formulate the compounds of the present invention as a tumor-growth-inhibiting, anticancer compound, or antimicrobial, known surface active agents, excipients, smoothing agents, suspension agents and pharmaceutically acceptable film-forming substances and coating assistants, and the like may be used. Preferably alcohols, esters, sulfated aliphatic alcohols, and the like may be used as surface active agents; sucrose, glucose, lactose, starch, crystallized cellulose, mannitol, light anhydrous silicate, magnesium aluminate, magnesium methasilicate aluminate, synthetic aluminum silicate, calcium carbonate, sodium acid carbonate, calcium hydrogen phosphate, calcium carboxymethyl cellulose, and the like may be used as excipients; magnesium stearate, talc, hardened oil and the like may be used as smoothing agents; coconut oil, olive oil, sesame oil, peanut oil, soya may be used as suspension agents or lubricants; cellulose acetate phthalate as a derivative of a carbohydrate such as cellulose or sugar, or methylacetate-methacrylate copolymer as a derivative of polyvinyl may be used as suspension agents; and plasticizers such as ester phthalates and the like may be used as suspension agents. In addition to the foregoing preferred ingredients, sweeteners, fragrances, colorants, preservatives and the like may be added to the administered formulation of the compound produced by the method of the invention, particularly when the compound is to be administered orally.

In the case of using the anti-tumor, anti-cancer, or anti-microbial produced by methods of the invention as a biochemical test reagent, the compound produced by methods disclosed herein inhibits the progression of the disease when it is dissolved in an organic solvent or hydrous organic solvent and it is directly applied to any of various cultured cell systems. Usable organic solvents include, for example, methanol, methylsulfoxide, and the like. The formulation can, for example, be a powder, granular or other solid inhibitor, or a liquid inhibitor prepared using an organic solvent or a hydrous organic solvent. While a preferred concentration of the compound produced by the method of the invention for use as an anti-microbial, anti-cancer, or anti-tumor compound is generally in the range of about 1 to about 100 µg/ml, the most appropriate use amount varies depending on the type of cultured cell system and the purpose of use, as will be appreciated by persons of ordinary skill in the art. Also, in certain applications it may be necessary or preferred to persons of ordinary skill in the art to use an amount outside the foregoing range.

The following non-limiting examples are meant to describe the preferred methods of the invention using certain preferred embodiments of the invention. Variations in the details of the particular methods employed and in the precise chemical compositions obtained will undoubtedly be appreciated by those of skill in the art.

EXAMPLE 1

Fermentation Protocol for Production of the Compounds of Formulas (IV) and (V)

Strain NPS008187 was grown in a 40 ml tube containing 10 ml of seed medium consisting of the following per liter of sea water: starch, 10 g; yeast extract, 4 g; and peptone, 2 g. The culture was allowed to incubate for 3 days at 28 degree C. on a rotary shaker operating at 250 rpm. The vegetative culture was mixed with 2 ml of cryoprotective solution consisting of 500 g glycerol per liter of deionized water. 1.5 ml portions of this mixture were transferred to a sterile cryogenic tube (2 ml capacity). The vegetative cultures so obtained were frozen and stored at −80 degree C.

Seed culture for the production of NPS008187 compounds was prepared by transferring 1.5 ml of the cryopreservative culture to a 40 ml tube containing 10 ml of sterile seed medium having the same composition as the above. The seed culture was incubated at 28 degree C. for 3 days on a rotary shaker operating at 250 rpm. Five ml of this seed culture was inoculated into 500 ml flask containing 100 ml of the seed medium. The second seed cultures were incubated at 28 degree C. for 3 days on a rotary shaker operating at 250 rpm. Five ml each of the second seed culture was inoculated into ten 500 ml flasks containing 100 ml of the seed medium. The third seed cultures were incubated at 28 degree C. for 3 days on a rotary shaker operating at 250 rpm. Five ml each of the third seed culture was inoculated into the production medium having the same composition as the seed medium. The production culture was incubated at 28 degree C. for 7 days on a rotary shaker operating at 250 rpm. The culture broth was extracted with 10 liters of ethyl acetate. The extract was dried in vacuo. The dried extract was then processed for the recovery of the compounds of Formulas (IV) and (V).

EXAMPLE 2

Fermentation Protocol for Production of the Compound of Formula (VI)

Seed culture for the production of NPS008187 compounds was prepared by transferring 1.5 ml of the cryopreservative culture to a 40 ml tube containing 10 ml of sterile seed medium consisting of the following per liter of sea water: starch, 10 g; yeast extract, 4 g; and peptone, 2 g. The seed culture was incubated at 28 degree C. for 3 days on a rotary shaker operating at 250 rpm. Five ml of this seed culture was inoculated into 500 ml flask containing 100 ml of the seed medium. The second seed cultures were incubated at 28 degree C. for 3 days on a rotary shaker operating at 250 rpm. Five ml each of the second seed culture was inoculated into ten 500 ml flask containing 100 ml of the seed medium. The third seed cultures were incubated at 28 degree C. for 3 days on a rotary shaker operating at 250 rpm. Five ml each of the third seed culture was inoculated into the production medium consisting of the following per liter of sea water: starch 5 g; Hydro Solubles, 4 ml; Menhaden fish meal, 2 g; Kelp powder, 2 g; and chitosan, 2 g. The production culture was incubated at 28 degree C. for 4 days on a rotary shaker operating at 250 rpm. Sterile XAD-16 resin (~3 grams) was added to each flask. The flasks were returned to the shaker and incubated at 28 degree C. and 250 rpm for additional 3 days. The culture broth was filtered through cheese cloth to recover the cell mass and XAD-16 resin. The cell mass-resin was extracted with 10 liters of ethyl acetate. The extract was dried in vacuo. The dried extract, was then processed for the recovery of the compound of Formula (VI).

EXAMPLE 3

Purification of the Compounds of Formulas (IV) and (V)

The crude extract (4.2 g) of NPS008187 from Example 1 was dissolved in ethyl acetate and the polar components were extracted with water by liquid-liquid separation. The remaining ethyl acetate soluble portion was concentrated (3.3 g) and chromatographed on a flash C18 column (15 cm×40 mm ID) using a water/MeOH step gradient of 40%, 50%, 60%, 75%, 100% MeOH. The compounds of Formulas (IV) and (V) eluted in 75% MeOH. These fractions were further separated by preparative HPLC using the following conditions:

| | |
|---|---|
| Column: | Phenomenex Luna 10u C18 |
| Dimensions: | 25 cm × 21.2 mm ID |
| Flow rate: | 14.5 ml/min |
| Detection: | UV DAD |
| Solvent: | 60% ACN/H₂O for 14 min, 60% to 70% ACN in 14 min |

The flash C18 fraction enriched in pyrrolosesquiterpenes (166 mg) was dissolved in MeOH (16.6 ml). 500 uL aliquots of this solution were sequentially injected using the HPLC chromatography conditions described above which yielded three main peaks, an unknown compound, the compound of Formula (V), and the compound of Formula (IV) respectively.

The above fractions were further purified using a semi-preparative HPLC method described below:

| | |
|---|---|
| Column: | ACE 5 C18-HL |
| Dimensions: | 25 cm × 10.6 mm ID |
| Flow rate: | 3 ml/min |
| Detection: | UV DAD |
| Solvent: | Gradient of 35% ACN 65% H₂O to 80% ACN (14 min). |

The partially purified pyrrolosequiterpene natural products of formulas (IV) and (V) can be obtained as pure materials in small quantities by using the conditions described above.

EXAMPLE 4

Purification of the Compound of Formula (VI)

The crude extract (196 mg) from Example 2 was dissolved in MeOH (3.92 ml). 200 uL aliquots of this solution were sequentially injected using the HPLC chromatography conditions described below. The compound of Formula (VI) eluted at 8.5 min.

| | |
|---|---|
| Column: | Phenomenex Luna 10u C18 |
| Dimensions: | 60 cm × 21.2 mm ID |
| Flow rate: | 14.5 ml/min |
| Detection: | UV DAD |
| Solvent: | Gradient of 10% to 80% ACN in 7 min, 80% to 100% in 1 min, 100% ACN for 5 min. |

The formula (VI)-enriched fraction was further purified using a semi-preparative HPLC method described below:

| | |
|---|---|
| Column: | ACE 5 C18-HL |
| Dimensions: | 25 cm × 10.6 mm ID |
| Flow rate: | 3 ml/min |
| Detection: | UV DAD |
| Solvent: | Gradient of 50% to 80% MeOH/H₂O in 12 min, 5 min at 80% MeOH, 80% to 100% MeOH in 1 min then 14 min at 100% MeOH) |

Using the above conditions, the compound of Formula (VI) eluted at 21.5 min as a pure compound.

EXAMPLE 5

Structural Characterization

The compounds purified in Examples 3 and 4 were characterized by ¹H NMR, ¹³C NMR, HMQC, NOEDS, COSY and HMBC correlations, UV, and HRESIMS. Additionally, IR and specific rotation were obtained for Formula (V). UV, IR, specific rotation, and HRESIMS results are as follows:

Formula (IV): UV (Acetonitrile/H₂O) $\lambda_{max}$ 335, 285(sh) nm; HRESIMS m/z 318.2082 [M+H] $\Delta_{calc}$ $C_{19}H_{28}NO_3$ (318.2069)=4.0 ppm.

Formula (V): $[\alpha]^{22}_D$+16.8 (c 0.0002, MeOH); UV (Acetonitrile/H₂O) $\lambda_{max}$ 335, 285(sh) nm; UV (MeOH) $\lambda_{max}$ 333 (ε14,400), 285 (sh) (6,700) nm; IR (NaCl) $\nu_{max}$ 3400, 3270, 2970, 1635, 1608, 1572, 1450, 1400, 1314, 1114, and 1061 cm⁻¹; HRESIMS m/z 356.1841 [M+Na] $\Delta_{calc}$ $C_{19}H_{27}NO_4Na$ (356.1838)=0.9 ppm.

Formula (VI): UV (Acetonitrile/H₂O) $\lambda_{max}$ 335, 285(sh) nm; HRESIMS m/z 322.1792 [M+Na] $\Delta_{calc}$ $C_{19}H_{25}NO_2Na$ (322.1783)=2.7 ppm.

¹H NMR and ¹³C NMR assignments are presented in Tables 1 and 2 respectively with reference to the labeled structures below:

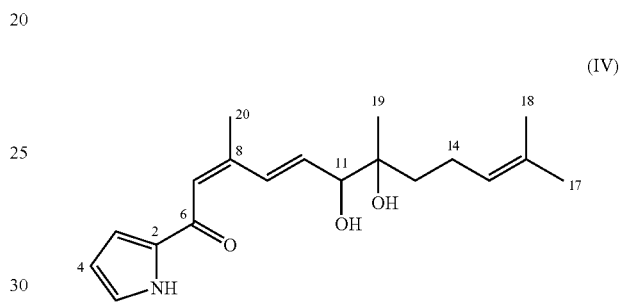

(IV)

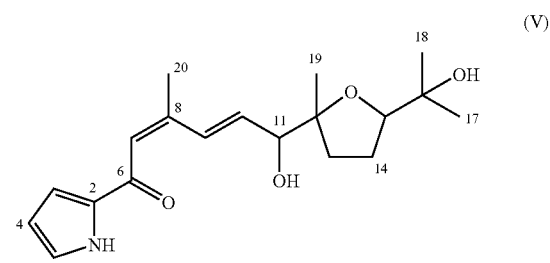

(V)

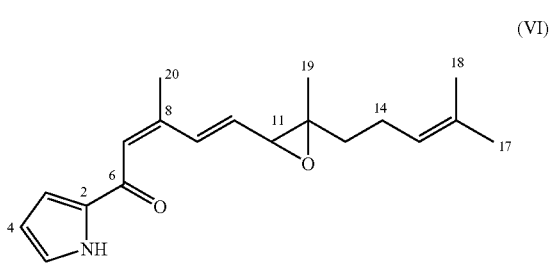

(VI)

TABLE 1

1H NMR Assignments

| atom no. | Formula (IV) *δ_H int., mult, J (Hz) | Formula (V) *δ_H int., mult, J (Hz) | Formula (VI) ±δ_H int., mult, J (Hz) |
|---|---|---|---|
| 1-NH | | | 11.77 1H, br s |
| 3 | 6.97 1H, br d, 3.8 | 6.97 1H, br dd, 3.8, 1.3 | 7.04 1H, br m |
| 4 | 6.22 1H, dd, 3.8, 2.1 | 6.22 1H, dd, 3.8, 2.2 | 6.20 1H, dt, 3.8, 2.2 |
| 5 | 7.05 1H, m | 7.05 1H, br dd, 2.2, 1.3 | 7.09 1H, m |
| 7 | 6.67 1H, br s, | 6.67 1H, br s | 6.75 1H, br s |
| 9 | 7.81 1H, d, 16.1 | 7.83 1H, d, 16.1 | 7.97 1H, d, 16.1 |
| 10 | 6.31 1H, dd, 16.1, 6.5 | 6.23 1H, dd, 16.1, 6.6 | 6.03 1H, dd, 16.1, 7.6 |
| 11 | 4.00 1H, d, 6.5 | 4.12 1H, dd, 6.6 | 3.38 1H, d, 7.6 |
| 13 | 1.56 1H, m | 2.13 1H, m | 1.64 1H, m |
|  | 1.44 1H, m | 1.62 1H, ddd, 11.6, 8.2, 3.1 | 1.47 1H, m |
| 14 | 2.08 2H, m | 1.87 1H, m | 2.05 2H, m |
|  |  | 1.82 1H, m |  |
| 15 | 5.11 1H, br t, 7.2 | 3.82 1H, dd, 9.5, 6.0 | 5.10 1H, br t, 7.2 |
| 17 | 1.65 3H, br s | 1.16 3H, s | 1.65 3H, s |
| 18 | 1.59 3H, br s | 1.14 3H, s | 1.57 3H, br s |
| 19 | 1.14 3H, s | 1.15 3H, s | 1.26 3H, s |
| 20 | 2.11 3H, s | 2.10 3H, br s | 2.06 3H, br s |

*δ_H values referenced to internal solvent for CD$_3$OD at 3.31 ppm
±δ_H values referenced to internal solvent for DMSO-d6 at 2.50 ppm

TABLE 2

13C NMR Assignments

| atom no. | Formula (IV) δ_C* mult. | Formula (V) δ_C* mult. | Formula (VI) δ_C± mult. |
|---|---|---|---|
| 2 | 135.4 s | 135.4 s | ND |
| 3 | 117.5 d | 117.5 d | 115.9 d |
| 4 | 111.2 d | 111.2 d | 109.8 d |
| 5 | 126.6 d | 126.6 d | 125.7 d |
| 6 | 182.2 s | 182.2 s | 179.5 s |
| 7 | 123.4 d | 123.5 d | 122.6 d |
| 8 | 149.9 s | 149.7 s | 146.8 s |
| 9 | 131.3 d | 131.2 d | 132.4 d |
| 10 | 138.0 d | 138.0 d | 132.8 d |
| 11 | 79.7 d | 78.9 d | 62.3 d |
| 12 | 75.5 s | 86.7 s | 63.1 s |
| 13 | 39.7 t | 34.7 t | 37.9 t |
| 14 | 23.0 t | 27.8 t | 23.3 t |
| 15 | 125.9 d | 88.6 d | 123.7 d |
| 16 | 132.1 s | 72.3 s | 131.2 s |
| 17 | 25.9 q | 26.3 q | 25.4 q |
| 18 | 17.7 q | 25.1 q | 17.5 q |
| 19 | 22.6 q | 23.9 q | 16.4 q |
| 20 | 21.4 q | 21.4 q | 20.6 q |

*δ_C values referenced to internal solvent for CD$_3$OD at 49.00 ppm
±δ_C values obtained through HSQC and HMBC and referenced to internal solvent for DMSO at 39.50 ppm
ND: Not detected A sesquiterpenoid side chain for the compound of Formula V was confirmed through a series of COSY and HMBC correlations as follows:

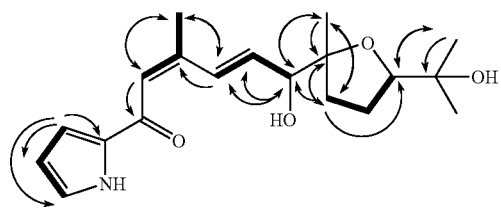

—continued

COSY
HMBC

The relative stereochemistry of the THF ring in the compound of Formula V was established by NOEDS analysis as follows:

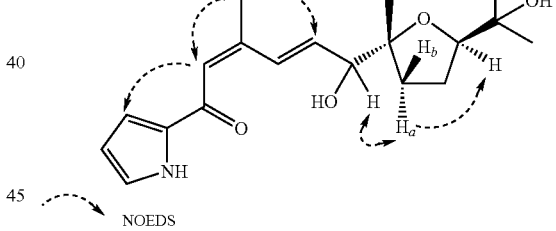

NOEDS

Irradiation of one of the H$_2$-13 methylene protons at δ$_H$ 2.13 (H$_a$-13) resulted in enhancements at H-15 and H-11, indicating that H-15 and the pentadienol side chain at C-12 are the same side of the THF ring. Therefore, the C-19 methyl group and the terminal dimethylcarbinol groups was determined to be on the other side of the THF ring. It was not possible to independently irradiate the H$_3$-17, H$_3$-19 and H$_3$-20 methyl protons due to near degeneracy, however simultaneous irradiation of all three methyl groups resulted enhancement of H$_b$-13.

Within the sesquiterpene side chain of the compound of Formula V, several substructures were defined, including two olefinic spin systems (H-7, H-8, H$_3$-20 and H-9, H-10, H-11) that were joined by HMBC correlations from H-9 to C-8 and C-20, effectively creating a methyl-pentadienol. In addition, a tetrahydrofuran ring substituted at the 2- and 5-positions with a methyl group and a terminal dimethylcarbinol was delineated through a series of COSY and HMBC correlations (H-13 and H-19 to C-12; H-13 and H-17 to C-15; H-15 to C-18). The tetrahydrofuran was joined to the pentadienol via corroborative HMBC correlations from H-11 to C12 and H-13 to C-11. The characterization of the sesquiterpenoid side chain was completed by joining C-7/C-8 olefin to the ketone carbonyl through an HMBC correlation from H-7 to C-6. While H-7 was not correlated to C-2 in the HMBC spectrum, a correlation was observed at H-3 upon irradiation of H-7 in an NOEDS experiment, establishing the connectivity between the pyrrole and its sesquiterpene side chain.

For the compound of Formula V, the geometries of the C-7/C-8 and C-9/C-10 double bonds were established through analysis of NOEDS experimental data and proton-proton coupling constants. Irradiation of the $H_3$-20 methyl proton resulted in enhancements at H-7 and H-10, supporting assignment of the Z-geometry for the C-7/C-8 olefin, while the H-9/H-10 coupling constant (J=16.1 Hz) was consistent with the E-geometry.

While the spectral data for the compound of Formula IV were similar to that of the compound of Formula V (Tables 1 and 2), the $^{13}C$ NMR spectrum for the compound of Formula IV contained signals corresponding to two olefinic carbons in place of signals corresponding to two carbons bearing oxygen. In addition, two methyl proton signals were downfield shifted ($\delta_H$ 1.65, s, $H_3$-17 and $\delta_H$ 1.59, s, $H_3$-18) while one of the methyl carbon signals was upfield shifted ($\delta_C$ 17.7, C-18). Together, these data suggested that the sesquiterpene side chain of the compound of Formula IV terminated in a typical dimethyl olefin. Complete analysis of the COSY, HMQC, and HMBC spectra indicated that the compound of Formula IV represented a C-11/C-12 diol.

The spectral data for compound of Formula VI compared favorably with that of the compound of Formula IV, with the exception that H-11 was shifted upfield from $\delta_H$ 4.00 to $\delta_H$ 3.38. In order to account for this observation, together with the additional degree of unsaturation and the loss of one oxygen atom when compared to the compound of Formula IV, the compound of Formula VI was determined to be the epoxide.

EXAMPLE 6

Growth Inhibition of Human Colorectal Adenocarcinoma, HT-29 cells

HT-29 (ATCC; HTB-38) a human colorectal adenocarcinoma cell line was maintained in complete McCoy's 5A medium (McCoy's 5A medium supplemented with 10% (v/v) Fetal bovine serum, 2 mM glutamine, 10 mM HEPES, 1% (v/v) non-essential amino acids (NEAA), 1 mM sodium pyruvate and Penicillin/Streptomycin at 100 IU/ml and 100 µg/ml respectively). The cells were cultured in an incubator at 37° C. in 5% $CO_2$ and 95% humidified air.

For cell growth inhibition assays, HT-29 cells were seeded at $5\times10^3$ cells/well in 90 µl complete media into Corning 3904 black-walled, clear-bottom tissue culture plates and the plates were incubated overnight to allow cells to establish and enter log phase growth. Two independent assays were performed using 200 mM or 400 mM stock solutions prepared in 100% DMSO. 10× concentrated serial dilutions of the compound of Formula (V) were prepared in appropriate culture medium. Ten µl volumes of the serial dilutions were added to the test wells in triplicate resulting in final concentrations ranging from 500 µM to 158 nM or 1 mM to 7.81 µM. The plates were returned to the incubator for 48 hours. The final concentration of DMSO was 0.25% in all samples.

Following 48 hours of drug exposure, 10 µl of 0.2 mg/ml resazurin (obtained from Sigma-Aldrich Chemical Co.) in $Mg^{2+}$, $Ca^{2+}$ free phosphate buffered saline was added to each well and the plates were returned to the incubator for 3-6 hours. Since living cells metabolize Resazurin, the fluorescence of the reduction product of Resazurin was measured using a Fusion microplate fluorometer (Packard Bioscience) with $\lambda_{ex}$ =535 nm and $\lambda_{em}$=590 m filters. Resazurin dye in medium without cells was used to determine the background, which was subtracted from the data for all experimental wells. The data were normalized to the average fluorescence of the cells treated with media +0.25% DMSO (100% cell growth) and $EC_{50}$ values (the drug concentration at which 50% of the maximal observed growth inhibition is established) were determined using a standard sigmoidal dose response curve fitting algorithm (XLfit 3.0, ID Business Solutions Ltd). The result is indicated in Table 3.

EXAMPLE 7

Growth Inhibition of Murine Melanoma, B16-F10 Cells

B16-F10 (ATCC; CRL-6475) a murine melanoma cell line was maintained in complete Dulbecco's Modification of Eagle's Medium (DMEM) (DMEM supplemented with 10% (v/v) Fetal bovine serum, 2 mM glutamine, 10 mM HEPES and Penicillin/Streptomycin at 100 IU/ml and 100 µg/ml respectively). The cells were cultured in an incubator at 37° C. in 5% $CO_2$ and 95% humidified air.

For cell growth inhibition assays, B16-F10 cells were seeded at $1.25\times10^3$ cells/well in 90 µl complete media into Corning 3904 black-walled, clear-bottom tissue culture plates and the plates were incubated overnight to allow cells to establish and enter log phase growth. Two independent assays were performed using 200 mM or 400 mM stock solutions prepared in 100% DMSO. 10× concentrated serial dilutions of the compound of Formula (V) were prepared in appropriate culture medium. Ten µl volumes of the serial dilutions were added to the test wells in triplicate resulting in final concentrations ranging from 500 µM to 158 nM or 1 mM to 7.81 µM. The plates were returned to the incubator for 48 hours. The final concentration of DMSO was 0.25% in all samples.

Following 48 hours of drug exposure, 10 µl of 0.2 mg/ml resazurin (obtained from Sigma-Aldrich Chemical Co.) in $Mg^{2+}$, $Ca^{2+}$ free phosphate buffered saline was added to each well and the plates were returned to the incubator for 3-6 hours. Since living cells metabolize Resazurin, the fluorescence of the reduction product of Resazurin was measured using a Fusion microplate fluorometer (Packard Bioscience) with $\lambda_{ex}$ =535 nm and $\lambda_{em}$=590 nm filters. Resazurin dye in medium without cells was used to determine the background, which was subtracted from the data for all experimental wells. The data were normalized to the average fluorescence of the cells treated with media +0.25% DMSO (100% cell growth) and $EC_{50}$ values (the drug concentration at which 50% of the maximal observed growth inhibition is established) were determined using a standard sigmoidal dose response curve fitting algorithm (XLfit 3.0, ID Business Solutions Ltd). The result is indicated in Table 3.

TABLE 3

| $EC_{50}$ values of the compound of Formula (V) against HT-29 and B16-F10 cells | | |
|---|---|---|
| | HT-29 | B16-F10 |
| $EC_{50}$ (µM) | 286 | 260 |

The EC$_{50}$ values indicate that the compound of Formula (V) was able to inhibit the growth of HT-29 and B16-F10 tumor cells.

EXAMPLE 8

Antimicrobial Assays

Minimum inhibitory concentrations (MICs) were determined according to the National Committee for Clinical Laboratory Standards (NCCLS) susceptibility test guideline M7-A5 (Ferraro, M. 2001 Methods for Dilution Antimicrobial Susceptibility Tests for Bacteria that Grow Aerobically; Approved Standard (NCCLS). National Committee for Clinical Laboratory Standards (NCCLS), Villanova, which is incorporated herein by reference in its entirety). Antimicrobial data for the compound of Formula (V) is shown in Table 4.

TABLE 4

Antimicrobial MIC values for the compound of Formula (V).

| Organism | MIC (µg/ml) |
| --- | --- |
| Staphylococcus aureus - MSSA | 64 |
| Bacillus cereus 14579 | 72 |
| Escherichia coli imp | 128 |
| Candida albicans | >128 |

The compound of Formula (V) was shown to possess antibacterial activity versus the gram positive microorganisms tested.

EXAMPLE 9

Pharmaceutical Formulations

1) Formulations Administered Intravenously by Drip, Injection, or the Like

Vials containing 5 g of powdered glucose are each added aseptically with 10 mg of a compound of Formulas (I)-(VI) and sealed. After being charged with nitrogen, helium or other inert gas, the vials are stored in a cool, dark place. Before use, the contents are dissolved in ethanol and added to 100 ml of a 0.85% physiological salt water solution. The resultant solution is administered as a method of inhibiting the growth of a cancerous tumor in a human diagnosed as having such a tumor or as a method of treating bacterial infection in a human diagnosed as having such an infection. The solution is administered at between approximately 10 ml/day to approximately 1000 ml/day, intravenously, by drip, or via a subcutaneous or intraperitoneal injection, as deemed appropriate by those of ordinary skill in the art.

2) Formulation to be Administered Orally Or The Like

A mixture obtained by thoroughly blending 1 g of a compound of Formulas (I)-(VI), 98 g of lactose, and 1 g of hydroxypropyl cellulose is formed into granules by any conventional method. The granules are thoroughly dried and sifted to obtain a granule preparation suitable for packaging in bottles or by heat sealing. The resultant granule preparations are orally administered at between approximately 100 ml/day to approximately 1000 ml/day, depending on the symptoms, as deemed appropriate by those of ordinary skill in the art of treating cancerous tumors or bacterial infection in humans.

The examples described above are set forth solely to assist in the understanding of the invention. Thus, those skilled in the art will appreciate that the methods may provide derivatives of compounds.

One skilled in the art would readily appreciate that the present invention is well adapted to carry out the objects and obtain the ends and advantages mentioned, as well as those inherent therein. The methods and procedures described herein are presently representative of preferred embodiments and are exemplary and are not intended as limitations on the scope of the invention. Changes therein and other uses will occur to those skilled in the art which are encompassed within the spirit of the invention.

It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions indicates the exclusion of equivalents of the features shown and described or portions thereof. It is recognized that various modifications are possible within the scope of the invention. Thus, it should be understood that although the present invention has been specifically disclosed by preferred embodiments and optional features, modification and variation of the concepts herein disclosed may be resorted to by those skilled in the art, and that such modifications and variations are considered to be falling within the scope of the invention.

What is claimed is:

1. A compound selected from the group consisting of the structure of Formula (I) and pharmaceutically acceptable salts thereof:

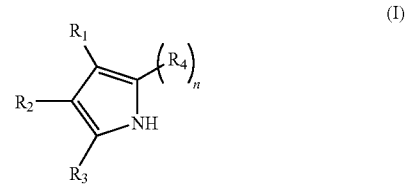

wherein $R_1$, $R_2$, and $R_3$ are separately selected from the group consisting of a hydrogen atom, halogen atom, mono-substituted, poly-substituted and unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, and halogenated alkyl including polyhalogenated alkyl;

wherein $(R_4)_n$ is a multiple-unit chain and wherein $R_4$ for the first unit is:

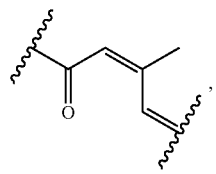

$R_4$ for the second unit is an isoprene selected from the group consisting of:

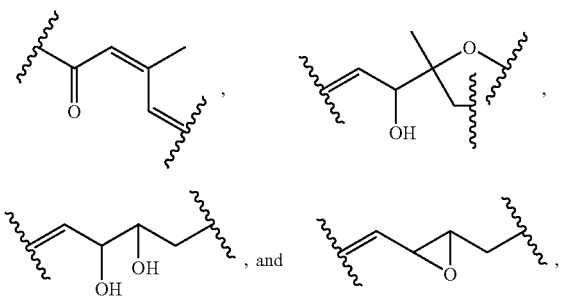

and $R_4$ for the third unit is an isoprene selected from the group consisting of:

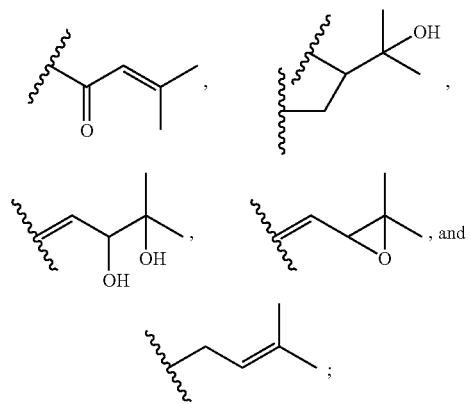

wherein n is 3.

2. The compound of claim 1 selected from the group of structures consisting of:

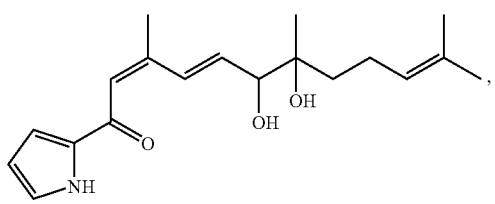

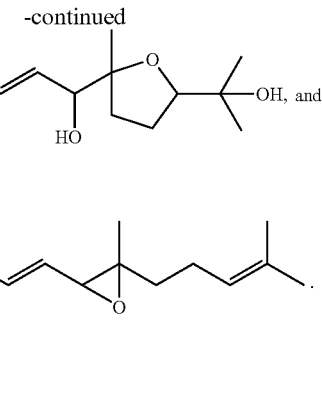

3. A compound selected from the group consisting of the structure of Formula (I) and pharmaceutically acceptable salts thereof:

(I)

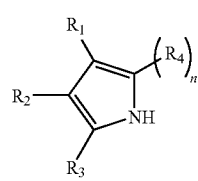

wherein $R_1$, $R_2$, and $R_3$ are separately selected from the group consisting of a hydrogen atom, halogen atom, mono-substituted, poly-substituted and unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, and halogenated alkyl including polyhalogenated alkyl;

wherein $(R_4)_n$ is a multiple-unit chain and $R_4$ for the first unit is:

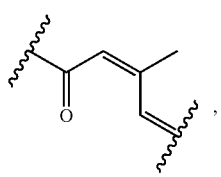

$R_4$ for the second unit has the structure of Formula (IA)

(IA)

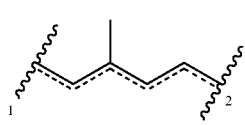

and is functionalized with at least one of hydroxy, oxo, epoxy, ether, and cyclic ether, and $R_4$ for the third unit has the structure of Formula (IA):

(IA)

and is optionally functionalized with hydroxy, oxo, epoxy, ether, and cyclic ether and wherein $R_4$ for the second and third units is attached to the previous unit via either attachment point 1 or 2;

wherein n is 3;

wherein a bond represented by a dashed and solid line is either a carbon-carbon single bond or a carbon-carbon double bond; and any bond represented by a dashed and solid line that is a carbon-carbon double bond has a configuration selected from the group consisting of cis and trans.

4. The compound of claim 3 wherein $R_1$, $R_2$, and $R_3$ are hydrogen.

5. The compound of claim 4 selected from the group of structures consisting of:

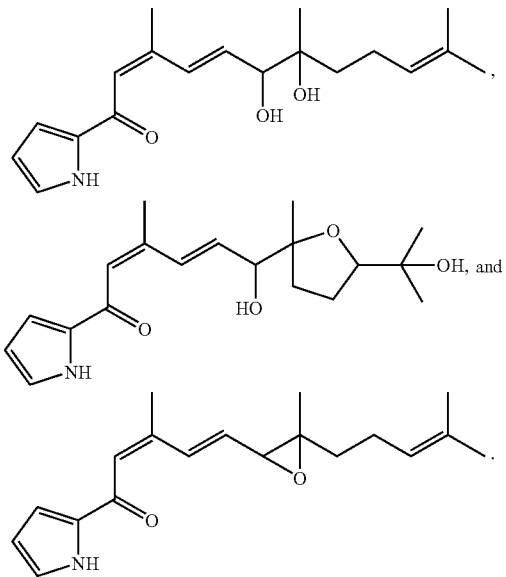

6. A compound selected from the group consisting of the structure of Formula (II) and pharmaceutically acceptable salts thereof:

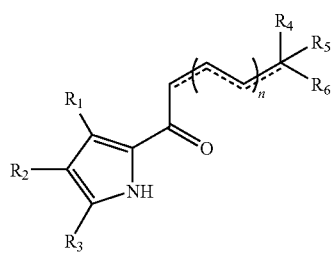

(II)

wherein $R_1$, $R_2$, and $R_3$ are separately selected from the group consisting of a hydrogen atom, halogen atom, mono-substituted, poly-substituted or unsubstituted variants of the following residues: saturated $C_1$-$C_{24}$ alkyl, unsaturated $C_2$-$C_{24}$ alkenyl and $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, and halogenated alkyl including polyhalogenated alkyl;

$R_4$, $R_5$, and $R_6$ are separately selected from the group consisting of a hydrogen atom, halogen atom, methyl, and hydroxy or are separately absent;

wherein each repeated unit n is optionally functionalized with methyl, hydroxy, oxo, epoxy, ether, or cyclic ether wherein at least one repeated unit n is functionalized with at least one hydroxy, oxo, epoxy, ether, or cyclic ether.

wherein n is 4;

wherein a bond represented by a dashed and solid line is either a carbon-carbon single bond or a carbon-carbon double bond; and any bond represented by a dashed and solid line that is a carbon-carbon double bond has a configuration selected from the group consisting of cis and trans.

7. The compound of claim 6 wherein $R_1$, $R_2$, and $R_3$ are hydrogen.

8. The compound of claim 7 selected from the group of structures consisting of

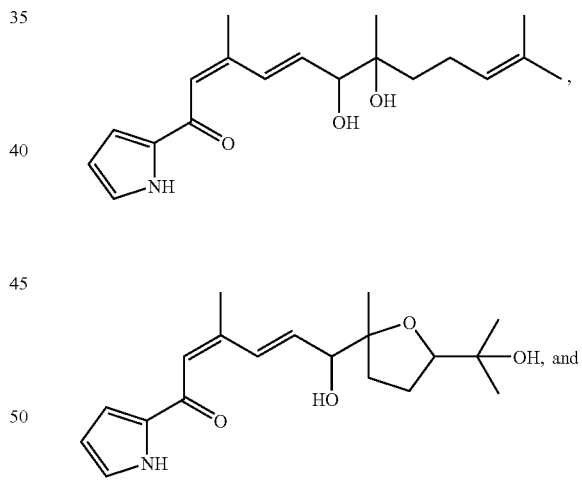

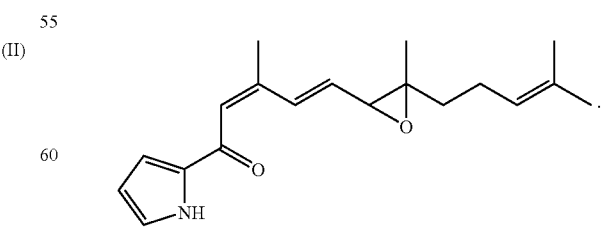

9. A compound selected from the group consisting of the structure of Formula (III) and pharmaceutically acceptable salts thereof:

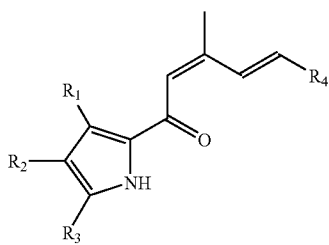

(III)

wherein $R_1$, $R_2$, and $R_3$ are separately selected from the group consisting of a hydrogen atom, halogen atom, mono-substituted, poly-substituted and unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkyithjo, arylthio, oxysulfonyl, carboxy, cyano, and halogenated alkyl including polyhalogenated alkyl; and wherein $R_4$ is a seven carbon alkyl or alkenyl functionalized with at least one methyl group and one or more hydroxy, oxo, epoxy, ether, or cyclic ether groups.

10. The compound of claim 9 wherein $R_4$ is selected from the group of structures consisting of:

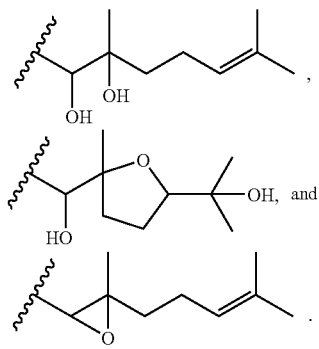

11. The compound of claim 10 wherein $R_1$, $R_2$, and $R_3$ are hydrogen.

* * * * *

UNITED STATES PATENT AND TRADEMARK OFFICE
CERTIFICATE OF CORRECTION

PATENT NO.         : 7,550,604 B2
APPLICATION NO.    : 11/205605
DATED              : June 23, 2009
INVENTOR(S)        : Venkata Rami Reddy Macherla Page 1 of 1

It is certified that error appears in the above-identified patent and that said Letters Patent is hereby corrected as shown below:

At item 56, page 1, column 2, line 11, please delete "conjugafum,"" and insert --conjugatum,"--.

At item 56, page 1, column 2, line 13, please delete "Biotekhnol" and insert --Biotechnol--.

At column 1, line 44, please delete "Chlamidia," and insert --chlamydia--.

At column 12, line 22 (approx.), please delete "perfluromethyl," and insert --perfluoromethyl,--.

At column 16, line 40, please delete "intreperitoneally," and insert --intraperitoneally--.

At column 23, line 8, please delete "14 min" and insert --14 min.--.

At column 23, line 25, please delete "pyrrolosequiterpene" and insert --pyrrolosesquiterpene--.

At column 23, line 57 (approx.), please delete "MeOH)" and insert --MeOH).--.

At column 29, line 37, please delete "Intravenously" and insert --Intravenously,--.

At column 34, line 20, in claim 6, please delete "ether." and insert --ether,--.

At column 35, line 23 (approx.), in claim 9, please delete "alkyithjo," and insert --alkylthio,--.

Signed and Sealed this
Twenty-seventh Day of September, 2011

David J. Kappos
*Director of the United States Patent and Trademark Office*